United States Patent [19]

Rutter

[11] 4,012,433
[45] Mar. 15, 1977

[54] PROCESS FOR MANUFACTURING 4-CHLORO-2-BUTYNYL m-CHLOROCARBANILATE

[75] Inventor: Jerry L. Rutter, Overland Park, Kans.

[73] Assignee: Gulf Oil Corporation, Pittsburgh, Pa.

[22] Filed: Nov. 24, 1975

[21] Appl. No.: 634,575

[52] U.S. Cl. .......................................... 260/471 C
[51] Int. Cl.² ....................................... C07C 125/06
[58] Field of Search ............................... 260/471 C

[56] References Cited

UNITED STATES PATENTS

| 3,155,713 | 11/1964 | Hopkins et al. | 260/471 C |
| 3,226,426 | 12/1965 | Hopkins et al. | 260/471 C |

FOREIGN PATENTS OR APPLICATIONS

| 1,133,716 | 7/1962 | Germany | 260/633 |
| 1,135,893 | 9/1962 | Germany | 260/633 |

OTHER PUBLICATIONS

Kittila, *Dimethylformamide Chemical Uses*, pp. 81–84 (1967).

*Primary Examiner*—Jane S. Myers
*Attorney, Agent, or Firm*—Carl A. Cline

[57] ABSTRACT

In the process for manufacturing 4-chloro-2-butynyl m-chlorocarbanilate (the herbicide barban) from the corresponding 4-hydroxy-2-butynyl m-chlorocarbanilate it has been discovered that yields and product quality are improved by employing dimethylformamide as reaction promoter in combination with thionyl chloride or phosgene as chlorinating agent.

3 Claims, No Drawings

PROCESS FOR MANUFACTURING 4-CHLORO-2-BUTYNYL m-CHLOROCARBANILATE

DESCRIPTION OF THE INVENTION

BACKGROUND

In the process for manufacturing the herbicide barban it is desirable to avoid use of 4-chloro-2-butyn-1-ol as a reagent. Therefore, as disclosed in U.S. Pat. No. 3,155,713 a preferable manufacturing procedure employs as a final step the substitution of chlorine for the hydroxy group of 4-hydroxy-2-butynyl N-(3-chlorophenyl) carbamate. The use of thionyl chloride as chlorinating reagent is disclosed in the patent. U.S. Pat. No. 3,226,426 discloses use of thionyl chloride in combination with pyridine to give an 83.6 percent yield of crude reaction product. Although this method admittedly is not free from side reactions and the product contains various impurities, still overall results are better than are obtained with other reagent systems which are available for replacement of hydroxy groups with chlorine. The presence of carbamate structure in the molecule, which may react with chlorinating agents, presents a difficult problem and severely limits the choice of reagent systems.

In the chlorination of a simple acetylenic alcohol, as for example, 2-butyne-1,4-diol, a much simpler situation exists with respect to possible side reactions, so that a greater variety of chlorinating reagents may be used, including reagents which are more effective. Yields of better than 90 percent have been disclosed in German Pat. Nos. 1,133,716 and 1,135,893 in reaction of butynediol and propargyl alcohol with the reagent system consisting of thionyl chloride or phosgene in combination with dimethylformamide. This reagent system is unique in some respects. It is known, for example, that dimethylformamide and thionyl chloride form an adduct which can be isolated (M. D. Scott and H. Spedding, *J. Chem. Soc.* 1968 p. 1603–1609). I have discovered that this very active reagent system may be used to replace the hydroxy group on 4-hydroxy-2-butynyl m-chlorocarbanilate in better yields and with less formation of by-products than the more gentle reagent systems which have been employed in the past.

SUMMARY

Briefly, I have discovered that in the process for manufacturing 4-chloro-2-butynyl N-(3-chlorophenyl) carbamate a substantial improvement is obtained in both yield and product quality by means of the step comprising reacting 4-hydroxy-2-butynyl N-(3-chlorophenyl)carbamate with thionyl chloride or phosgene in combination with a reaction promoting quantity of dimethylformamide.

DETAILED DESCRIPTION

In a commercial process for preparation of 4-chloro-2-butynyl N-(3-chlorophenyl)carbamate (barban), the corresponding 4-hydroxy-2-butynyl carbamate ester is treated with thionyl chloride in the presence of pyridine as catalyst. This procedure yields a product mixture which requires a filtration step to remove substantial quantities of amorphous substances which interfere with flow of fluid through the filter. Analyses by high pressure liquid chromatography (HPLC) of the barban obtained in the commercial procedure indicates conversions below 90 percent.

In the complete absence of catalyst, moreover, a decidedly inferior product is obtained in the barban process. Analysis of the latter material shows a lower conversion to barban (approximately 46%) and the presence of a significant quantity of unidentified components, presumably allenic rearrangement products.

The presence of the carbamate function, which is known to be sensitive to heat and to acid and base treatment, apparently complicates the chlorination reaction. The conversion of 2-butyne-1,4-diol to its dichloro analog with thionyl chloride in the presence of catalytic amounts of pyridine, by comparison, can be accomplished in virtually quantitative yields.

When dimethylformamide is substituted for pyridine in the barban process, several advantages are realized — (1) analyses of the technical barban thus produced generally indicate a barban content in excess of 90 percent and occasionally quantitative conversion is approached; (2 a by-product which originates in an earlier step, disappears to a large extent, as HPLC analyses for this substance fall to as low as one-fourth of their former levels; (3) the residue obtained in the previously mentioned filtration step amounts to only one-third to one-fourth of its former quantity; (4) the latter residue is much more highly crystalline, facilitating a more rapid filtration operation.

The amount of chlorinating agent required to effect the chlorination of the hydroxycarbamate should be at least a molar equivalent of the amount of the latter substance, although 5 to 10 percent in excess of a molar equivalent of the chlorinating agent is not detrimental. The quantity of dimethylformamide employed as a reaction promoter is quite critical. Although catalytic effects result from use of trace amounts, optimum conversion is obtained when the dimethylformamide is added in a quantity which is the range of 0.20 to 0.80 percent of the weight of 4-hydroxy-2-butynyl N-(3-chlorophenyl)carbamate charged. Although the rate of the chlorination reaction can be increased when the amount of dimethylformamide is increased (e.g., to 3.7 percent, 5 percent or 10 percent), the conversion to the chloro compound declines as a result and the production of impurities increases.

Catalysis by dimethylformamide is not specific to thionyl chloride in this reaction; a quantitative conversion to technical barban was achieved when an equimolar amount of phosgene was employed to effect the chlorination. The product thus obtained was of high quality, equivalent to that observed in the dimethylformamide catalyzed thionyl chloride reactions.

The solvent of choice appears to be ethylene dichloride (EDC) but excellent conversions are obtained in ethyl acetate, chloroform, and in a 50:50 mixture of EDC 1,2-dimethoxymethane.

In the following illustrative procedures there are described the chlorination of 4-hydroxy-2-butynyl N-(3-chlorophenyl)carbamate with and without the conventional catalyst and in Examples 1 and 2, the improved procedure of the present invention.

1. Chlorination of Hydroxycarbamate Without Catalyst.

To a warm (65°) stirred solution of 60 g (0.025 mole) of 4-hydroxy-2-butynyl N-(3-chlorophenyl) carbamate in 75 ml of ethylene dichloride (EDC) was added a solution of 1.9 ml of thionyl chloride in 25 ml of EDC over a period of 2 minutes. The system was heated at 64° for a period of 17 hours, during which a slow evolution of gas occurred. Evaporation of solvent afforded 6.1 g of dark viscous oil; the NMR spectrum of the latter substance exhibited excessive signals when compared to the spectrum of the authentic material. Analysis by HPLC: barban — 45.8% (w/w) biscarbamate — 1.6% (w/w), with additional unidentified components present.

warm solution of 4-hydroxy-2-butynyl N-(3-chlorophenyl)carbamate in 75 ml of EDC was added dropwise over a period of 60 minutes. After 17 hours at 65°, the solvent was evaporated to afford 6.5 g of barban which was analyzed by HPLC: barban — 97.5% (w/w), biscarbamate — 1.0% (w/w); bisurea — 1.6% (w/w).

The results of these three procedures are summarized in Table 1.

TABLE 1

PREPARATION OF BARBAN USING THIONYL CHLORIDE

| Reaction Conditions | | | | Product Analyses, % (w/w) | | | |
|---|---|---|---|---|---|---|---|
| Time | Temp. | Catalyst | Molar Scale | barban | Biscarbamate | Bis urea | Procedure number |
| 17 hr | 64° | pyridine | 0.05 | 77.9 | 6.2 | 0.9 | 2 |
| 17 hr | 64° | pyridine | 0.05 | 88.5 | 4.2 | 1.6 | 2 |
| 17 hr | 65° | pyridine | 0.025 | 90.9 | 6.3 | 1.5 | 2 |
| 17 hr | 65° | none | 0.025 | 45.8 | — | 1.6 | 1 |
| 17 hr | 65° | dimethylformamide | 0.025 | 96.6 | 1.3 | 1.2 | Ex. 1 A |
| 17 hr | 65° | dimethylformamide | 0.025 | 97.6 | 2.2 | 1.2 | B |
| 17 hr | 65° | dimethylformamide | 0.025 | 97.5 | 1.0 | 1.2 | C |

2. Chlorination of Hydroxycarbamate with Pyridine Catalyst.

A warm (64°) solution of 12.0 g (0.050 mole) of 4-hydroxy-2-butynyl N-(3-chlorophenyl)carbamate ad 44 μl (5.610⁻⁴ mole) of pyridine in 44 ml of EDC was stirred while thionyl chloride (3.8 ml, 0.05 mole) was added over a period of 10 minutes. The reaction mixture was heated at 64° 17 hours. Evaporation afforded a dark oil which crystallized on standing and amounted to 13.1 g. Analysis by HPLC: barban — 88.5% (w/w), biscarbamate — 4.2% (w/w), bisurea — 1.6% (w/w). The results of this and other pyridine catalyzed runs are summarized in Table 1.

EXAMPLE 1

Chlorination of Hydroxycarbamate with Dimethylformamide Catalyst

A. A solution of 4-hydroxy-2-butynyl N-(3-chlorophenyl)carbamate (6.0 g., 0.025 mole) and 23 μl of dimethylformamide in 75 ml of EDC was stirred at 65° while a solution of 1.9 ml (0.025 mole) of thionyl chloride in 25 ml of EDC was added dropwise over a period of 60 minutes. The reaction mixture which resulted was stirred at 65° for a total of 17 hrs. Evaporation of solvent afforded 6.5 g of product which was analyzed by HPLC: barban — 96.6% (w/w); biscarbamate — 1.3% (w/w); bisurea — 1.2% (w/w).

B. In another preparation on the same scale, the thionyl chloride and dimethylformamide in 25 ml of EDC were stirred at 65° while a warm solution of 4-hydroxy-2-butynyl N-(3-chlorophenyl)carbamate in 75 ml of EDC was added dropwise over 60 minutes. Barban (6.5 g) was obtained by evaporation of the solvent after 17 hours at 65° and analyzed by HPLC: barban 97.6% (w/w); biscarbanate — 2.2% (w/w); bisurea — 1.6% (w/w).

C. In another procedure on the same scale, the thionyl chloride in 25 ml of EDC was stirred at 65° while a

EXAMPLE 2

Chlorination of Hydroxycarbamate with Phosgene-Dimethylformamide

To a warm (50°) stirred solution of 4-hydroxy-2-butynyl N-(3-chlorophenyl)carbamate (59.9 g., 0.500 mole) and dimethylformamide (0.6 g) in 150 ml of EDC was added 250 ml of 12.5% phosgene in benzene over a period of about 30 minutes. The reaction mixture was heated at 50° for 4.5 more hours, then at 60° for 2 hours. Evaporation of solvent afforded a quantitative yield of technical barban.

I claim:

1. In the process for manufacturing 4-chloro-2-butynyl N-(3-chlorophenyl)carbamate from 4-hydroxy-2-butynyl N-(3-chlorophenyl)carbamate, the improvement comprising reacting 4-hydroxy-2-butynyl N-(3-chlorophenyl)carbamate wtih a chlorinating agent selected from the group consisting of thionyl chloride and phosgene in the presence of a reaction-promoting amount of dimethylformamide.

2. In the process for manufacturing 4-chloro-2-butynyl N-(3-chlorophenyl)carbamate from 4-hydroxy-2-butynyl N-(3-chlorophenyl)carbamate, the improvement comprising reacting one hundred parts by weight 4-hydroxy-2-butynyl N-(3-chlorophenyl)carbamate with a molar equivalent quantity of a chlorinating agent selected from the group consisting of thionyl chloride and phosgene in the presence of 0.20 to 0.80 parts by weight of dimethylformamide.

3. In the process for manufacturing 4-chloro-2-butynyl N-(3-chlorophenyl)carbamate by reacting one hundred parts by weight 4-hydroxy-2-butynyl N-(3-chlorophenyl)carbamate with a molar equivalent quantity of a chlorinating agent consisting essentially of thionyl chloride in ethylene dichloride reaction medium, the improvement comprising carrying out the reaction in the presence of from 0.20 to 0.80 parts by weight of dimethylformamide.

* * * * *